United States Patent [19]

Chvapil

[11] Patent Number: 5,078,744
[45] Date of Patent: Jan. 7, 1992

[54] METHOD OF USING TENDON/LIGAMENT SUBSTITUTES COMPOSED OF LONG, PARALLEL, NON-ANTIGENIC TENDON/LIGAMENT FIBERS

[75] Inventor: Milos Chvapil, Tucson, Ariz.

[73] Assignee: Bio-Products, Inc., Tuscon, Ariz.

[21] Appl. No.: 411,230

[22] Filed: Sep. 22, 1989

Related U.S. Application Data

[63] Continuation of Ser. No. 93,018, Sep. 4, 1987, abandoned.

[51] Int. Cl.$^5$ ................................. A61F 2/08
[52] U.S. Cl. ............................. 623/13; 128/DIG. 8
[58] Field of Search .................... 623/13; 128/DIG. 8

[56] References Cited

U.S. PATENT DOCUMENTS

| | | | |
|---|---|---|---|
| 4,149,277 | 4/1979 | Bokros | 623/13 |
| 4,455,690 | 6/1984 | Homsy | 623/13 |
| 4,605,414 | 8/1986 | Czajka | 623/13 |
| 4,668,233 | 5/1987 | Seedhom et al. | 623/13 |
| 4,703,108 | 10/1987 | Silver et al. | 128/DIG. 8 X |

FOREIGN PATENT DOCUMENTS 8500511  2/1985  World Int. Prop. O. ............ 623/13

OTHER PUBLICATIONS

Orthopaedic Society for Sports Medicine, Annual Meeting, 1983 in Williamsburg, Va., Percy et al.

Primary Examiner—Randall L. Green
Assistant Examiner—Paul Prebilic
Attorney, Agent, or Firm—Cahill, Sutton & Thomas

[57] ABSTRACT

A method of repairing connective tissue uses a heterograft for supporting ingrowth of ligament or tendon connective tissue to replace damaged connective tissue in a subject which is composed of a plurality of long, thin fibers extracted from animal connective tissue having generally the same mechanical properties as the tissue to be replaced. The individual fibers are extracted by a sequence of chemical treatments and mechanical treatments, purified to eliminate foreign material from the fibers, and cross-linked to a degree that causes their shrinkage temperature to have a preselected value that corresponds to the desired tensile strength, allows only a preselected amount of water retention by the fibers in order to enhance attraction of fibrogenic cells to the fiber surfaces, and avoids producing foreign body reaction to the heterograft. The fibers are maintained generally parallel in a bundle or weave. The tensile strength of the heterograft permits the subject to continue normal activities involving the joint immediately after implant surgery without immobilizing the joint. This ensures that repetitive, normal stress is applied to the heterograft and aligns ingrowing fibrogenic cells and natural collagen connective tissue replacement produced by the fibrogenic cells in the direction of the repetitive stresses, orienting and enhancing the growth of natural replacement connective tissue.

19 Claims, 3 Drawing Sheets

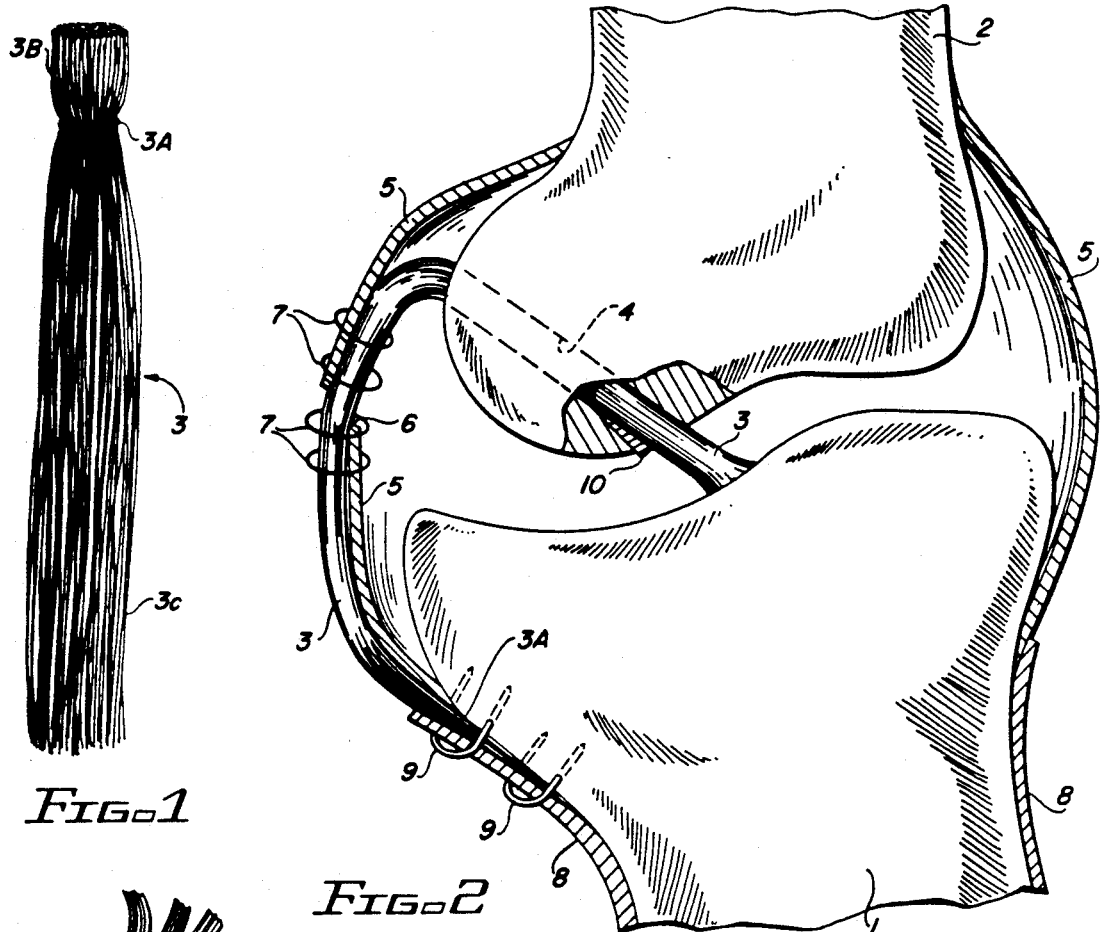
FIG. 1
FIG. 2
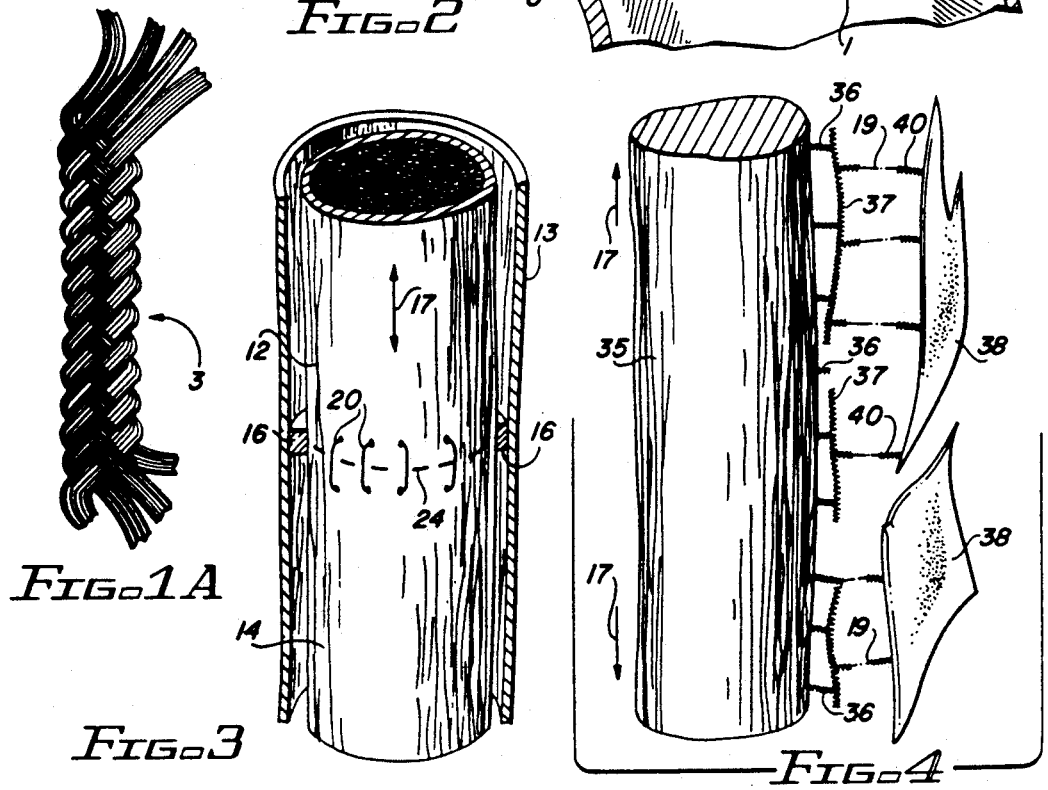
FIG. 1A
FIG. 3
FIG. 4

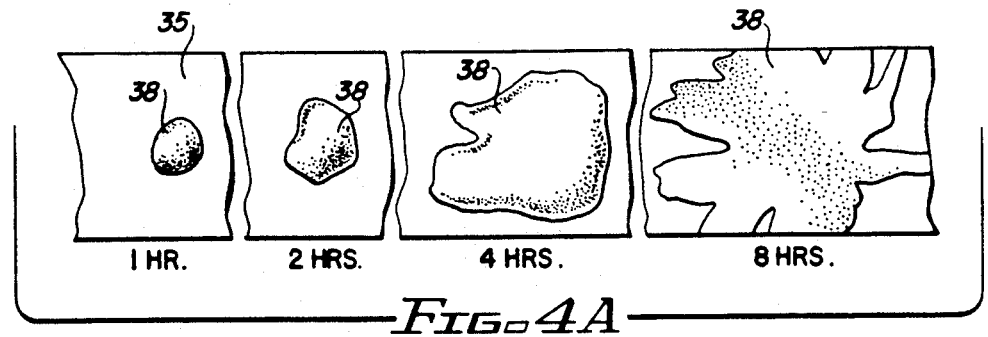
FIG. 4A
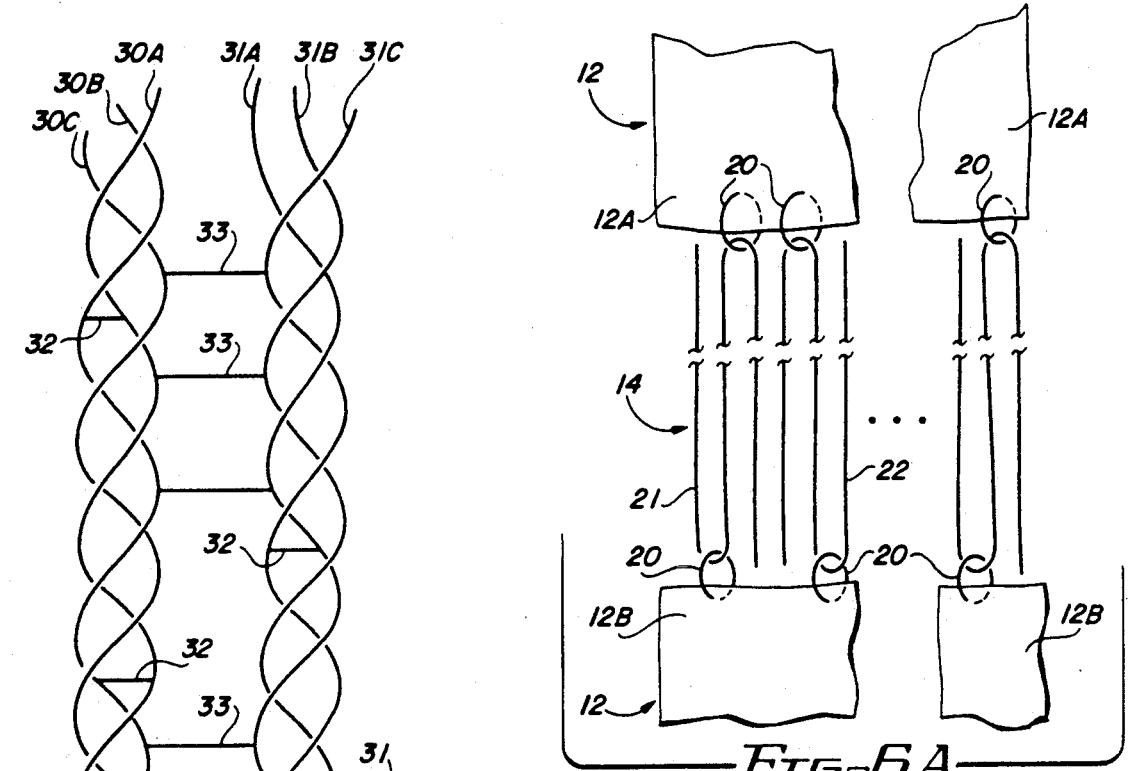
FIG. 6A
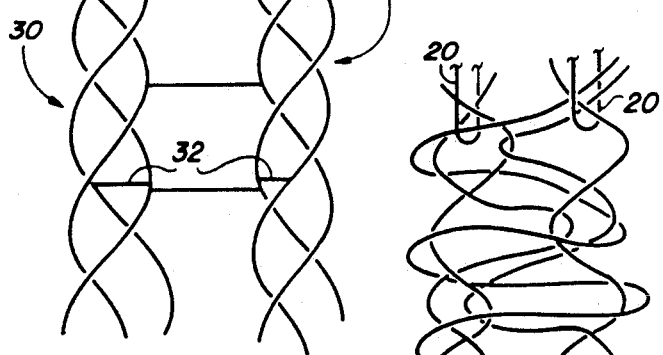
FIG. 5
FIG. 6B

METHOD OF USING TENDON/LIGAMENT SUBSTITUTES COMPOSED OF LONG, PARALLEL, NON-ANTIGENIC TENDON/LIGAMENT FIBERS This is a continuation of application Ser. No. 093,018, filed Sept. 4, 1987, now abandoned by Milos Chvapil and entitled "TENDON/LIGAMENT SUBSTITUTES COMPOSED OF LONG, PARALLEL, NON-ANTIGENIC TENDON/LIGAMENT FIBERS".

BACKGROUND OF THE INVENTION

The invention relates to improved techniques for providing tendon or ligament implants that promote regrowth tendon or ligament tissue without immobilizing an associated joint.

Great progress has been made in the replacement of various organs/tissues by homografts, heterografts, and allografts, using either the approach of implanting a non-resorbable permanent substitute of the injured or missing parts using metallic or plastic materials, or by implantation of biodegradable "scaffold" material which serves as a temporary matrix for cell and blood vessel ingrowth. Substitution or repair of tendons and ligaments has been more difficult than substitution or repair of other organs. For example peritendinous adhesions that prevent sliding of a tendon in its sheath may be formed during healing of tendons by ingrowth of fibroblasts into an implant. Numerous polymers and tendon grafts have been tested, but a review of the literature shows no satisfactory solution of the ligament/tendon replacement problem. It is clear that only a few materials can be used to obtain high mechanical strength and simultaneously achieve fast cell ingrowth into a ligament/tendon implant matrix. Most polymers that have been tested do not allow good "association" or junction with the tissue being repaired. Prior implants that provide adequate mechanical strength suffer from the shortcoming that they fail to function well enough as substrates for fibrogenic cell migration to be viable ligament/tendon substitutes. Such materials have poor, weak "association" with the repair tissue. The anastomosis of prior implanted tendon prosthesis to an injured tendon stump or to muscle or bone has created many problems because such anastomosis cannot resist large mechanical stresses without slipping or cutting of sutures through the implanted tendon prosthesis. Furthermore, artificial ligament and tendon substitutes generally have been unsatisfactory because they have been subject to loss of mechanical strength or fragmentation due to fatigue caused by cyclic loading. Also, artificial ligament and tendon substitutes usually have produced chronic inflammatory reactions.

For long it has been known that cadaver tendons/ligaments would be ideal substitutes for injured tendons/ligaments if their antigenicity could be overcome.

Collagen hemostatic felt has been implanted as a ligament and tendon substitute. This is described in the paper "Pure Collagen as a Ligament and Tendon Substitute: A Histological Analysis in Animals", by E. C. Percey, John Medlen, and the present inventor Milos Chvapil, presented by John Medlen at the 1983 annual meeting of the Orthopedic Society of Sports Medicine at Williamsburg, Va.

However, there still is a need for an improved ligament/tendon implant that provides adequate mechanical strength immediately after the implantation, promotes rapid regrowth of ligament/tendon tissue without inflammatory reaction, and which can fulfill various other requirements for the repair/replacement of tendons and ligaments in humans.

SUMMARY OF THE INVENTION

Accordingly, it is an object of the invention to provide an improved ligament/tendon substitute that provides adequate mechanical strength, promotes rapid regrowth of ligament/tendon tissue without inflammatory reaction, and which can fulfill various other requirements for the repair/replacement of tendons and ligaments in humans.

It is another object of the invention to provide a technique for repairing or replacing ligaments and tendons, which can meet FDA requirements for approval of the technique for use in human subjects.

Briefly described, and in accordance with one embodiment thereof, the invention provides a graft, specifically a heterograft, for replacing damaged connective tissue, including a plurality of long, thin connective animal tissue fibers extracted from an animal tendon or ligament, purified to eliminate foreign materials from the fibers, and cross-linked to a degree that causes the shrinkage temperature of the fibers to have a preselected value, avoids producing of "foreign body reaction" to the fibers, and allows only a preselected amount of water retention by the fibers in order to enhance attraction of fibrogenic cells to the fiber surface. The fibers are maintained in a bundle in generally parallel relationship to each other, the number of fibers being such that the tensile strength of the heterograft permits the subject to continue normal activities involving the joint in which the heterograft is implanted immediately after implant surgery without immobilizing the joint. This ensures that repetitive normal stress is applied to the heterograft and thereby aligns ingrowing fibrogenic cells and natural collagen connective tissue replacement produced by the cells in the direction of the repetitive stress, thereby orienting and enhancing the growth of natural replacement connective tissue. In the described embodiments of the invention, the individual fibers are extracted from bovine Achilles tendons, and are extracted using a sequence of alternate chemical and mechanical compression treatments to obtain bovine tendon fibers having a length in the range from 8 to 30 centimeters and a thickness of 50 to 100 microns are utilized. Cross-linking with hexamethylenediisocyanate or by monomeric glutaraldehyde is described to achieve shrinkage temperatures in the range from 78° to 82° Centigrade. The compliance of the heterograft is approximately the same as that of the damaged connective tissue to be replaced, so "normal" stretching of the heterograft occurs and results in normal stressing of regrowing connective tissue produced by ingrowing fibrogenic cells which have the capacity to control the tension of the collagenous implant. This enhances proper alignment, tension and regrowth of the replacement connective tissue. In one embodiment of the invention, the fibers of the heterograft are arranged to produce loops at at least one end of the heterograft, thereby allowing sutures to be passed through the loops to anastomize the heterograft to a stump of the damaged connective tissue. In another embodiment of the invention, the fibers of the heterograft are woven into a weave that closely approximates the natural weave of bundles of fibers of the damaged connective tissue to be replaced. This results in optimum orientation of the regrown connective tissue. In the described examples, during the implant procedure the heterograft is soaked in a source of fibronectin and fibroblasts growth factor or other drugs before suturing it to tendon stumps or passing it through holes drilled through bones of a knee joint to replace or repair a ligament such as an anterior cruciate ligament. In the described examples, the heterograft is coated with or seeded with autologous tenoblasts obtained from the subject's body to accelerate ingrowth of fibrogenic tissue along the fibers of the heterograft.

BRIEF DESCRIPTION OF THE DRAWINGS

FIG. 1 is a plan view of a ligament or tendon implant composed of individual, purified long, generally parallel animal ligament or tendon fibers tied together at one end.

FIG. 1A is a plan view of an implant similar to the one of FIG. 1 except that it is braided.

FIG. 2 is a diagram illustrating the implant of FIG. 2 used to repair or replace an anterior cruciate ligament.

FIG. 3 is a partial sectional diagram illustrating use of the implant of FIG. 1 to repair a tendon in a peritendinous sheath.

FIG. 4 is a diagram useful in explaining how collagen fibers function as a substrate for propagation of fibrogenic cells.

FIG. 4A is another diagram useful in explaining how a collagen fiber promotes propagation of fibrogenic cells.

FIG. 5 is a diagram useful in explaining cross-linking.

FIG. 6A is a diagram illustrating the structure of a long collagen fiber implant structure which facilitates anastomosis of the implant with ligament/tendon stumps.

FIG. 6B is a diagram illustrating anastomosis of an implant formed of a textile-like weave of long ligament/tendon fibers.

DESCRIPTION OF THE PREFERRED EMBODIMENTS

Figure 7:
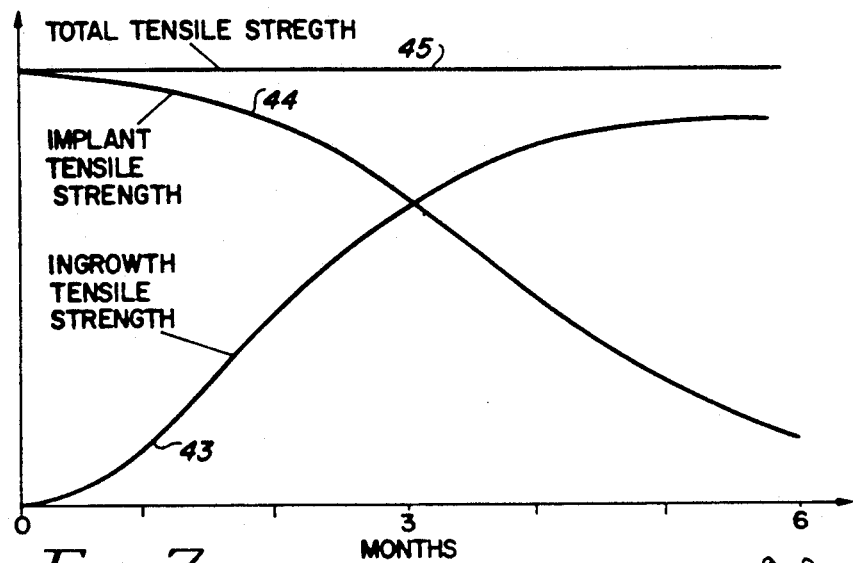
FIG. 7 is a diagram illustrating the decrease in implant tensile strength and accompanying increase in tensile strength of regenerated ligament/tendon tissue over a six month period.

Before describing the ligament/tendon implant of the present invention, it may be helpful to first discuss a number of requirements that I believe to be important for any ligament/tendon implant of the type that induces regrowth of ligament or tendon tissue.

First, immobilization of joints of a subject after the implanting procedure is undesirable because immobilization permits atrophying of ligament, tendon, cartilage, and muscle tissue. More importantly, joint immobilization prevents appropriate cyclic stressing of the regrowing ligament or tendon tissue. I believe that such cyclic stressing substantially enhances the regrowth of ligament/tendon tissue. High tensile strength of a ligament/tendon implant therefore is highly desirable. Swelling or shrinking of the implant material after the implant surgery must be minimal because swelling can cause the implant to occupy more space than is available. If an implant starts swelling after the implantation surgery, the swelling could dislodge a joint, or the implant could become highly compressed between joints which will not yield. Such compression would prevent ingrowth of fibrogenic cells. Shrinking can cause excessive tension in the implant. Preferably, the implant should not swell or shrink by more than about 5 percent.

No peritendinous adhesions should be formed where a tendon implant is fastened to bone or tendon stumps because peritendinous adhesions prevent free movement of the tendon in its peritendinous sheath. The implant must be chemically inert to prevent inflammation. The implant material should have large surface area fibers having characteristics that attract growth of fibrogenic tissue. The implant should be biodegradable so as to be resorbed at a rate that corresponds to the growth and increased strength of ingrowing ligament or tendon tissue. The compliance or elasticity of the implant should match that of the replaced ligament/tendon to allow suitable cyclic stressing of the ingrowing ligament/tendon tissue.

It is well established that collagen fibers are the best substrates for ingrowth, adhesion, and migration of fibroblasts. It also is known that polymers coated by collagen become "seeded", i.e., attract growth of fibroblasts, chondroblasts, etc. For example, see "Patterns of Three-dimensional Growth in Vitro in Collagen-coated Cellulose Sponge: Carcinomas and Embryonic Tissues", by J. Leighton, R. Mark and G. Justh, Cancer Research, 28:286, 1968 and "Enhancement of Healing in Osteochondral Defects by Collagen Sponge Implants" by D. P. Speer, M. Chvapil, R. G. Volz and M. D. Holmes, Clinical Orthopedics, 144:326, 1979. However, collagen coatings of polymer fibers generally are resorbed within a few days or a week, after which fibroblast propagation becomes retarded and disorganized. For example, collagen sponge inserted in articular cartilage is known to enhance fibroblasts and chondrocytes more rapidly than similar sponge made of polyvinylalcohol. See the above Clinical Orthopedics Article.

It is well-known that platelets have a high affinity for collagen. Fibrogenic cells generally have a high affinity to a collagen substrate in the presence of fibronectin, which is a cell surface membrane protein that recognizes and binds to certain amino acid sequences in collagen polypeptide. In accordance with the present invention, if a collagenous matrix of an implanted ligament or tendon with high surface area presented by individual longitudinally oriented fibers is used as a substrate for ingrowth of fibrogenic cells such as tenoblasts from an injured tendon stump, those cells will begin producing their own collagen and glycosaminoglycans.

These cells and the collagen produced by them will be effectively aligned and "remodeled" in the direction of longitudinal mechanical stress applied to the implant. This is why it is important not to immobilize a joint in which a ligament or tendon substitute is implanted, and why the implant should have compliance or elasticity very similar to that of the ligament or tendon being replaced. Then a normal amount of cyclic mechanical stress can be applied to the regrowing ligament or tendon to enhance its growth.

The invention described herein solves the problems of the prior art by providing an implant containing long, thin, chemically purified, compliant ligament/tendon fibers extracted from an animal ligament/tendon having the same general mechanical properties as a substitution for an injured human ligament/tendon. The animal ligament/tendon is disintegrated using various known procedures to obtain long, individual, parallel fibers that are up to 30 centimeters long and have thicknesses of 50 to 100 microns. For some applications, such as anastomosis (connection) to a severed ligament/tendon stump, the individual animal ligament/tendon fibers are braided, woven or otherwise processed to provide end loops through which sutures can pass and be retained. An example is given hereinafter to describe the purification of the animal ligament or tendon fibers. My unique purification and cross-linking process results in a highly pure collagenous ligament/tendon "implant" material wherein foreign cells such as contaminating non-collagenous proteins are removed. Several examples of cross-linking by biocompatible tanning agents are given to describe how to obtain an excellent, high tensile strength, non-antigenic collagen substrate for rapid, organized cell ingrowth. The substrate implant material is cross-linked to a degree necessary to achieve shrink temperatures ($T_s$) that result in resorption of the implant not sooner than three to five months after the implant surgery, and allow continued, rapid organized ingrowth of tenoblasts, fibroblasts, etc. by causing the tensile strength of the fibers to be approximately four to eight kilograms per square millimeter.

I have found that seeding autologous tenoblasts from other portions of the subject's body onto the implant accelerates new deposition of collagen and other products of the cells' activity onto the collagen fiber surface and decreases the time required for ligament/tendon regrowth by approximately ten days. Before the planned surgery a small segment of a tendon or ligament from the patient patellar ligament is removed under sterile conditions and in small pieces cultivated in tissue culture media. Tenoblasts grow, migrate from the tendon fragments and multiply with time of incubation. These cells then are harvested and injected into the scaffold formed by a sterile tendon or ligament implant consisting of the long, aligned, fine collagen fibers.

Referring now to FIG. 1, an implant 3 is composed of a bundle of long, thin collagen fibers that have been individually processed to purify them and remove them from a young adult bovine ligament or tendon. The bundle of fibers is tied together at location 3A by means of a short piece of the same kind of fiber to assure alignment and prevent knotting of fibers during the purification process. Numeral 3B indicates a short portion of each of the fibers above the tie 3A, and numeral 3C indicates the long lower portion of the fibers. Each of the fibers is 50 to 100 microns in diameter and can be as long as 20 to 30 centimeters.

The manner in which I purified the fibers and cross-linked them to control their tensile strength, elasticity, biodegradability or amount of time required for resorption, and swelling also is described subsequently. Before giving specific examples, however, it may be helpful to refer to FIGS. 2 and 3, which illustrate how the implant 3 of FIG. 1 is utilized as a ligament substitute and a tendon substitute, respectively. In FIG. 2, a lateral incision 6 is made in the periarticular connective tissue 5 connected to the femur 2 and the tibia 1 of a knee joint, in order to allow access to a torn anterior cruciate ligament which is to be repaired or regrown. If the lower portion of the anterior cruciate ligament is to be left attached to the tibia 1, the upper portion of the ligament is excised. A hole 4 is drilled through a portion of the tibia in alignment with the direction of the original anterior cruciate ligament, as indicated by dotted lines. The upper end portion 3B of implant 3 then is fed through the drilled hole 4 from its lower end. The lower end of the implant 3 is sutured to the stump of the anterior cruciate ligament. The excess portion of implant 3 extending out of the upper end of drilled hole 5 is folded downward, passed through the incision 6, and inserted beneath the periosteum 8 of tibia 1. Sutures 7 connect the periarticular connective tissue 5 to the adjacent portion of implant 3. Staples 9 attach the extremities of the implant 3 to the tibia 1 beneath the periosteum 8. A bone wedge 10 is driven into the lower end of drilled hole 4 to anchor implant 3. Alternately, if the entire anterior cruciate ligament is excised, another hole aligned with hole 4 is drilled in the upper portion of the tibia 1. The implant 3 then is passed through both holes, and is stapled at both ends to the tibia 1. A bone wedge 10 is driven into the lower end of drilled hole 4 to anchor implant 3.

FIG. 3 shows a tendon 12 surrounded by a peritendinous sheath 13. In normal movement, tendon 12 slides smoothly in the direction of arrows 17 within peritendinous sheath 13. Tendon 12 has been damaged, and severed as indicated by dotted line 24. An incision (not shown) is made in the sheath 13, and implant 14 of FIG. 1 is sutured at its upper end to the severed portion 24 of tendon 12 by means of sutures 25. The incision in sheath 13 then is sutured.

Reference numerals 16 designate a peritendinous adhesion of the junction 24 to the peritendinous sheath 13. Such peritendinous adhesions prevent proper movement of the tendon 12 and implant 14 in sheath 13 in the direction of arrows 17, and therefore must be minimized so that they are easily broken. Irritation of tendon tissue will produce peritendinous adhesions. Any surgical procedure on tendon 12 also will produce peritendinous adhesions. If such peritendinous adhesions can be minimized and kept tiny, they can be ruptured easily during the joint movement so that they do not prevent proper sliding of the tendon 12 within the peritendinous sheath 13.

FIG. 6A shows a structure that illustrates how implant 14 is effectively sutured to the tendon stumps 12A and 12B. Each individual long, thin tendon fiber 12 is doubled back on itself twice, thereby forming a loop at the upper end of the implant and another loop at the lower end of the implant. The sutures 20 then can pass through such loops, ensuring effective anastomosis of implant 14 to tendon stumps 12A and 12B. Alternately, implant 14 can be formed by braiding or weaving the long, thin collagen fibers, using an appropriate textile-like weave that produces a large number of strong loops throughout the implant. FIG. 1A shows a heterograft 3 wherein smaller bundles of ligament/tendon fibers are braided. The sutures 20 then can pass through and be strongly retained in such loops and strongly join the ends of implant 14 to tendon stumps 12A and 12B, ensuring effective anastomosis, which is very important since the implant is subjected to tension produced both by the initial surgical fixation, and later by myofibroblast shrinkage as fibroblast ingrowth and alignment occur along the implant fibers, which serve as an attractive substrate for fibrogenic cell propagation, as subsequently explained.

The long, thin collagen fibers having the same general mechanical properties as the tendon or ligament to be repaired or replaced are bundled or braided into the shape of the required implant. Ingrowth of fibroblasts, tenoblasts, or synovial cells into the implant is enhanced by coating the resulting arrangement of ligament or tendon fibers with fibronectin contained in the subject's blood or with commercially available growth factors, specifically with fibroblast growth factor or angiogenesis promoting factor available from AMGEN of California or from GENOTEC. These substances such as fibronectin, fibroblast growth factor or angiogenesis factor can be incorporated into the final tendon/ligament implant by simple dipping of the implant into a solution of such factors. In this case, these substances are loosely linked and are adsorbed on the collagen fibers. They may be "washed away" by body fluids before their full benefit is realized. If a stronger bond between the collagen and the factor is needed, it can be provided by a chemical linkage that can be formed by any one of various known methods, such as by carbodiimide reaction, or by forming a strong covalent linkage through glutaraldehyde. Such chemical bonding secures the retention and hence the effect of the factor within the implant for a longer time, thus creating a form of drug delivery system, without interfering with the function of the fibroblast growth factor, angiogenesis, or fibronectin.

In some cases I have seeded the implant with autologous tenoblasts taken from the subject's skin, etc.

The collagen fibers initially obtained from a bovine ligament or tendon are manufactured into the size, length, and with mechanical characteristics of the tissue to be replaced in order to provide implant elasticity or compliance similar to that of the damaged ligament or tendon to be repaired or replaced. Purification of the fibers is achieved during disintegration of the animal ligament or tendon material into the long, thin collagen fibers, which then are further purified and cross-linked to obtain a product composed of pure collagen, with toxic residues from the cross-linking agent being eliminated. The bundle of fibers is sufficiently strong after the purification and cross-linking procedures to enable the subject to carry on with normal activity such as walking, use of a hand containing a repaired tendon, etc. immediately after the surgical implant procedure. The resulting normal cyclic loading and stressing of the implant combined with its natural elasticity, results in cyclic stressing of ingrowing fibrogenic cells, resulting in rapid alignment thereof and rapid growth of properly aligned replacement tissue. The fibrogenic cells gradually resorb the implant at a rate that is compensated for by increasing of the strength of the ingrown ligament or tendon tissue.

At this point, before describing specific examples of the cross-linking procedure and our observed results of ligament and tendon regrowth on animals, it may be helpful to understand the mechanics of fibroblast propagation on collagen fibers and how normal cyclic stressing results in more rapid regrowth of high integrity replacement tissue and ultimately in resorption of the implant fiber itself.

Referring to FIG. 4, reference numeral 35 designates an individual animal ligament or purified, cross-linked tendon fiber of the implant. Various chemical "functional groups" 36, such as $NH_2$, COOH, and OH, extend from the purified collagen fiber surface. Reference numerals 38 designate fibroblasts that are growing and propagating on the collagen fiber substrate 35. For convenience of illustration, an exploded view is shown in FIG. 4, wherein dashed lines such as 19 indicate interaction of different chemical functional groups 40 of cell surface proteins, such as fibronectin of the fibroblasts 38, to effectuate attachment of fibroblast 38 to the collagenous substrate. However, the functional groups 40 of the surface membranes of fibroblasts 38 are not directly compatible with the functional groups 36 of the collagen substrate. Instead, they are compatible with a substance 37, known as fibronectin, contained in the subject's blood and tissue fluids and attached to various cell surfaces. Fibronectin is a glycoprotein that has a very high affinity to collagen surfaces, and contains chemical functional groups that act as receptors for both the functional groups 36 of the collagen fiber 35 and functional groups 40 of fibroblasts 38, and thereby indirectly make the collagen substrate 35 highly attractive to ligament or tendon fibroblasts such as 38. During the surgical implant procedure, the bundle of ligament or tendon fibers is dipped in the subject's blood, so that the fibers form the best possible substrate for propagation of fibrogenic cells (which can include fibroblasts or tenoblasts). Fibroblasts therefore rapidly become deposited on and propagate on collagen substrate 35.

FIG. 4A illustrates growth of fibroblasts 38 on collagen substrate 35 as a function of time, showing initial propagation of a tiny spherical "seed" 38 one hour after attachment to the substrate. After two hours, fibroblasts 38 have begun to flatten and spread out from its initial spherical shape. Before long, fibroblasts 38 and many others like them have joined and completely covered the surface of the collagen fiber. More fibroblasts then are formed on those already attached to the surface as rapid ingrowth of the fibroblasts progresses. The attached, propagating fibroblasts then produce new collagen material that forms new, regenerated ligament or tendon tissue around the original collagen substrate fiber 35. The products of the attached fibroblasts also act to slowly resorb the original purified collagen fiber 35. Thus, in a manner the original implant induces ligament/tendon substitution.

In accordance with the present invention, the sooner cyclic mechanical stretching of the elastic collagen fiber 35 occurs (which stretching is made possible by providing the implant with sufficiently high tensile strength to withstand normal physical activities by the subject), the sooner the attached, ingrowing fibroblasts and the new collagen tissue produced thereby become aligned in the direction of tensile forces 17 (FIG. 3) produced by the stretching. In addition to accelerated alignment, the mechanical stresses also increase the amount of collagen deposited by the stimulated fibroblasts. A hypothesis exists that mechanical stressing of a certain implant-cell composite induces an electrical field, which is stimulatory to the cells.

Next, it will be helpful to briefly describe the basics of cross-linking. A collagen fiber such as 35 is composed of numerous "basic collagen molecules", each basic collagen molecule being composed of three collagen molecules. In FIG. 5, a typical helical orientation of collagen chains 30 and 31 is shown. Thus, basic fibrillar 30 is composed of three chains each having a molecular weight of approximately 110,000. The collagen molecule composed of 30A, 30B, 30C and 31A, 31B, 31C, is approximately 3,000 Angstroms long and 15 Angstroms thick. Collagen in tissues always contains some cross-linking, both within individual chains as well as between individual collagen molecules, much of which cross-linking is loosened during the purification procedure. The cross-linking therefore must be replaced to restore and increase the structural strength of the collagen material before it can be used as a scaffolding for regrowth of ligaments or tendons. Cross-linking also regulates the rate of the resorption of the collagenous implant. Finally, cross-links reduce the already low antigenicity of the purified collagen fibers. In FIG. 5, reference numerals 33 designate intermolecular cross-links, and reference numeral 32 designates intramolecular cross-links.

Thus, increased cross-linking results in increased tensile strength of the collagen fibers, less swelling (i.e., less water retention), less biodegradability or resorbability of the collagen, and higher shrinkage temperature (shrinkage temperature being the temperature at which the collagen fibers contract).

Furthermore, if the cross-linking becomes too dense, ingrowth of fibrogenic tissue is inhibited. My experience has shown that shrinkage temperatures $T_s$ in the range of 78° to 82° Centigrade result in four to six months time for 80 to 90 percent resorption of the original ligament/tendon implant by the ingrown fibrogenic cells thereon. The reason that excessive cross-linking retards ingrowth of fibrogenic cells is that the fibrogenic cells prefer to adhere to and grow on hydrated collagen fiber, and a high degree of cross-linking prevents the collagen fibers from absorbing water. I have found that if the collagen substrate contains 30 to 45 percent water, increasing its volume by approximately 5 to 10 percent, it will be suitably pliable and will act as a optimum substrate for ingrowth of fibroblasts. Another effect of cross-linking is to regulate water content in the implanted collagen fiber ligament/tendon substitute.

FIG. 7 is a graph in which curve 44 generally designates the tensile strength of the ligament or tendon implant as a function of time, beginning with the time of the surgical implantation and ending six months later, when ligament/tendon regrowth is mostly complete. Curve 44 shows that the implant tensile strength is maximum at time 0, and has fallen to roughly 20 percent of its initial value six months later. Curve 43 indicates the tensile strength of the newly synthesized ligament or tendon that is being regenerated by rapidly ingrowing fibroblasts and oriented deposition of their products, which are structural macromolecules consisting of collagen and glycosaminoglycans. The tensile strength of the regrown collagen tissue initially is zero, and increases to nearly its final maximum value by the end of the six months. Line 45 generally designates the total strength of the "composite" ligament, that is, the sum of the decreasing tensile strength of the implant as it is being resorbed and the increasing tensile strength of the regenerated tissue as it is being formed. For success, it is essential that the total tensile strength 45 never be less than required for the prescribed, ordinary activities of the subject in the months after the implant procedure.

As the new ligament or tendon tissue is regenerated, repetitive, continued cyclic stressing or tensioning of the regrowing ligament or tendon has the effect of "remodelling" it, gradually adapting it to the structure of the original ligament or tendon which has been replaced or repaired.

Natural ligaments and tendons consist of bundles of collagen fibers which are not precisely parallel, but instead have a sort of "woven" structure. I believe that replacement and regrowth of ligaments and tendons can be optimized by providing implants composed of individual animal ligament or tendon fibers, as generally described above, woven into patterns that correspond quite closely to the natural "weave" of the bundles of collagen fibers of the original damaged ligament or tendon to be replaced or repaired. FIG. 8 illustrates this idea, wherein a portion of the implant 3 includes individual long, thin animal ligament/tendon fibers woven into a weave that closely approximates that of the natural ligament/tendon to be repaired/replaced. During the regrowth period, fibroblasts propagate along and adhere to the individual collagen fibers 35A-C, and produce replacement collagen fiber bundles such as 51A, 51B, and 51C which constitute the regrown ligament/tendon and have the desired "woven" pattern of the original ligament/tendon.

Figure 8A:
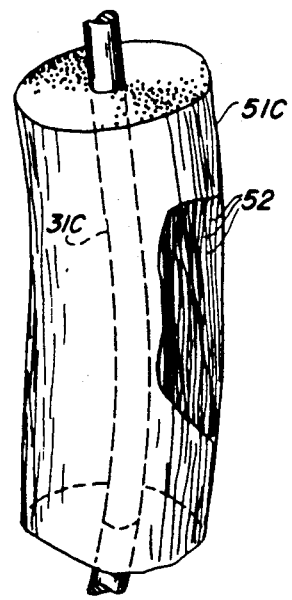
FIG. 8A is an enlarged partial cutaway view of one of the regrown ligament/tendon fiber bundles of FIG. 8.
Figure 8:
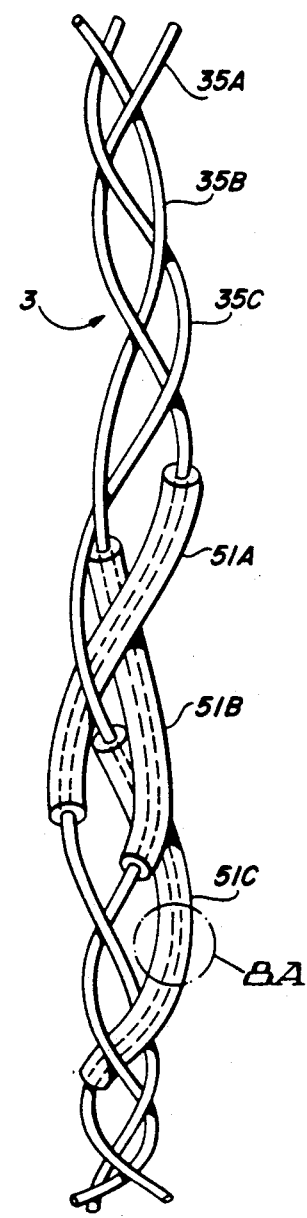
FIG. 8 is a diagram useful in explaining how a textile-like weave of long individual collagen fibers can result in a natural weave of regrown ligament/tendon fiber bundles.

FIG. 8A shows an enlarged partial cutaway view of collagen fiber bundle 51A, showing the individual generally parallel synthesized collagen fibers such as 52 that have been produced by the fibroblasts which have attached to and grown on implant ligament/tendon fiber 51C.

EXAMPLE 1

The aim of this example was to establish if pure, fine collagen fibers braided in a tendon-like structure serve as an adequate and temporary scaffold for fast ingrowth of connective tissue components. To this end, collagen fibers 50-100 microns thick and up to 30 centimeters long were isolated from adult bovine tendons, as described in Example 3. These were purified to remove cellular elements and all non-collagenous components, as described in Example 4. Fibers then were cross-linked to a high and medium cross-linking level with hexamethylenediisocyanate, as described in Example 5 to obtain fibers with lower density of cross-links (corresponding to a shrink temperature of 74° Centigrade) and high density of cross-links (corresponding to a shrink temperature of 82° Centigrade). The collagen fibers then were braided into a tendon prosthesis measuring approximately 3 millimeters in thickness, 7 millimeters in width, and 35-40 millimeters long. In adult roosters, the flexor superficialis and profundus tendons were excised and the two types ($T_s=74°$ C. and $T_s=82°$ C.) of tendon prosthesis were anastomosed to the proximal and distal stumps of the profundus. Twenty-eight legs of 14 adult roosters were used. Postoperatively, they were immobilized in plaster casts and harvested at two, three, five, and eight weeks post implantation.

The collagen fibers with a lesser degree of cross-linking served as a good substrate for fibroblastic ingrowth with no evidence of significant inflammatory or foreign body reaction. With increasing time after implantation, new vessels and collagen were found within the implant. The more highly cross-linked collagen fiber prostheses showed much slower cellular and vascular ingrowth, even after eight weeks, probably due to the inability of the highly cross-linked fibers to hydrate completely.

The examples show that highly purified and optimally cross-linked collagen fibers can serve as a tendon prosthesis that ultimately will become replaced by newly formed collagen.

EXAMPLE 2

Purified, long, thin collagen fibers were prepared according to Examples 3, 4, and 5 in the form of a braided ligament as shown in FIG. 1 for the replacement of an anterior cruciate ligament in a goat. The degree of cross-linking in the collagen fiber implant resulted in shrinkage temperatures of approximately 80° Centigrade. The implant was 1.3 cm wide, 0.8 cm thick, and 7.5 cm long and had tensile strength of 1200 to 1800 newtons. The extendibility at breaking was 5 to 7 percent of the original length. Five adult goats of both sexes, body weight 85 to 125 pounds, were used in the experiment. In one knee of each animal the cruciate ligament was removed and replaced with the collagen fiber implant. The opposite knee served as a nonoperative control. The surgical procedure was similar to that described previously (See "The Use of Carbon Fiber Implants in Anterior Cruciate Ligament Surgery" A. E. Strover et al., Clinical Orthopedics 196:88, 1985, incorporated herein by reference), except for the method of fixation to the bone. General anesthesia was achieved by endotracheal halothane. An anterolateral arthrotomy was used dislocating the knee cap medially. Through the same anterolateral incision access was gained to the posterolateral aspect of the femur to complete the femoral fixation. The intrapatellar fat pad and the ligamentum mucosusm was dissected from the anterior cruciate prior to removal of the latter and subsequently sutured to the collagen fiber implant following placement. A 4.65 mm drill was used to place tunnels in the tibia and femur with the hole alignment as nearly coinciding with the axis of the ligament as possible. The holes then were enlarged to 6.0 mm with a larger drill and their exits from the bone were rounded using dental burrs. Following preparation of the bone tunnel, the collagen fiber implant was passed through the tibia, across the joint space, and through the femur. Autologous bone wedges taken from the great trochanter of each animal were used to anchor the implants in their respective tunnels. Additional stabilization of the ligament was achieved by suturing "tails" of the ligament beneath the periosteum directly opposed to the bone, as shown in FIG. 2. Prior to placement of the wedges the ligament was tightened with the knee in 30 degrees of flexion. Following fixation of the ligament, the ligamentum mucosum and the fat pad were sutured to the implant. The joint was irrigated with normal saline and the capsule, retinaculum and skin closed in independent layers. Activity of the animal was allowed as tolerated.

The results of this study are summarized in Table 1.

weeks post-implantation, the prosthesis was completely covered with newly formed collagen structures, at six months the size and appearance of the anterior cruciate ligament substitute was not distinguishable from the collateral anterior cruciate ligament control.

The anterior cruciate ligament substitute was dissected and subjected to morphological and ultrastructural analysis. The data indicate an unique fast ingrowth of fibroblastic-spindle shaped cells and new vessels into the prosthesis. New collagen fibers of thinner diameter than that of control anterior cruciate ligament were deposited between the implanted collagen fibers. There were no abnormal cells or any evidence of increased reaction by morphological findings. It was found that at six months almost 80 percent of the original implanted anterior cruciate ligament prosthesis was resorbed and completely substituted by new structures mimicking the normal anterior cruciate ligament architecture. Although the mechanical characteristics of the implants were not tested, the clinical findings of a stable knee joint indicate that the implants functioned well as anterior cruciate ligament substitutes for the whole experimental period.

EXAMPLE 3—PREPARATION OF COLLAGEN FIBERS FROM RAW BOVINE TENDONS

Achilles tendons from cattle were collected and processed by alternating chemical and mechanical treatments to dissociate the individual fibers of the compact original tendon structure. The tendons were soaked for several days in 0.8 volume percent hydrochloric acid, and then mechanically compressed under high pressure by squeezing the material between rolling cylinders while continually narrowing the gap between the cylinders, obtaining more dissociation or disintegration of the tendon into individual fibers each time. The swollen fibers then were dehydrated by adding 20 percent NaCl, and washed and treated in excess volumes of 0.2 weight percent sodium hydroxide for several days, repeating the mechanical separation. The foregoing step then was repeated in an acidic environment with deswollen fibers in the presence of excess NaCl. The fibers obtained from each tendon were 50 to 100 microns in diameter, 20–30 centimeters in length, with a high content of salt, and a pH in the range of 3.0 to 3.5. The precise details of the procedure are as follows.

The tendons were fresh or frozen Achilles tendons from cattle 12 to 18 months old. The tendons were washed using tap water after cutting off ligaments, meat, and removing blood, and were drained overnight

TABLE 1

REVIEW OF RESULTS USING COLLAGEN FIBERS AS SUBSTITUTE OF ANTERIOR CRUCIATE LIGAMENT IN FIVE GOATS

| Goat # | Duration of Implantation (weeks) | Antibodies[e] Determination | Duration of Lameness[a] (weeks) | Knee Joint Stability[b] | % Implant Resorption[c] | % Implant Resplacement[d] |
|---|---|---|---|---|---|---|
| 1 | 6 | ND | 2 | 1.5 | 10–20 | 30 |
| 2 | 11 | ND | 3 | 1.5 | 50–60 | 60 |
| 3 | 12 | ND | 2 | 1.0 | 50–60 | 60 |
| 4 | 24 | ND | 2 | 1.5 | 80 | ~90 |
| 5 | 36 | ND | 2 | 1.5 | 100 | 100 |

[a]Lameness was evaluated daily by observing the spontaneous locomotion. After 14 days all patients walked without any visible deficit.
[b]Antero-posterior, lateral and rotational stability was evaluated at time of sacrifice and graded on a score from 1 to 4, 1 = normal, 2 = 0.5 cm loosening, 3 = 0.5–1.0 cm loosening, 4 = too loose.
[c,d]Information is based on morphological and scanning electron microsopy data.
[e]Serum analyzed for the presence of antibodies against type 1 bovine collagen by ELISA Method/ND refers to non detectable.

The data of Table 1 show that the goats were sacrificed 10 to 36 weeks postoperatively. The animals showed signs of lameness only during the first two weeks after the surgery, as they were not immobilized. However, at the time of sacrifice, the clinical evaluation of the stability of the operated knee joint showed no signs of being loose or unstable. During dissection of the anterior cruciate ligament already starting with 10 at about 4° Centigrade. The tendons contained about 30 percent dry substance, and included a fat content of about 3 percent. The original shrink temperature $T_s$ of the untreated tendon collagen was in the range from 60° to 62° Centigrade. A first alkali treatment of 0.3 weight percent calcium hydroxide and 0.1 weight percent sodium hydroxide was performed at a temperature below 25° Centigrade, slowly mixing the tendons for five to seven days. Tap water washing was performed for 10 minutes while mixing the tendons. The second alkali treatment of 1 percent sodium hydroxide and 0.1 percent hydrogen peroxide was performed under mixing conditions below 25° Centigrade wherein the ratio of tendon weight to solvent weight was 1 to 150. This was performed for 12 to 15 hours. At that time, the alkali swollen tendons were compressed under a pressure of about 1.5 atmospheres (i.e. about 21 pounds per square inch) between rubber rotating cylinders. The tendon material then was washed in tap water under mixing conditions for 30 minutes and drained for at least several hours. The dry substance content of the tendons at this point was approximately 20 percent. Next, an acid treatment was performed, wherein the tendons were incubated in a very slowly rotating drum containing a solution including 50 parts by weight water, 10 parts by weight concentrated HCL and 100 parts by weight tendon material; this was continued until the entire thickness of the swollen tendons was acidified, after approximately five hours. The tendon material then was washed in tap water under slow rotation. The pH of the final wash material was 2.8 to 3.0. The material was drained for several hours, at which time the dry substance content of the tendon material was approximately 14 percent. Dehydration of the material was performed in 20 weight percent solution of a NaCl under mixing conditions until the tendons were dehydrated throughout. A second acid treatment was performed by first washing the dehydrated and drained tendons under tap water. The pH was adjusted from to 2.8 to 3.0 until the tendons swelled to their original size, with a dry weight of 14 percent. The dehydration and second acid treatment steps were repeated three times, during which the tendons continue disintegrating into individual fibers, compressing the swollen tendon material between rubber rollers as necessary. The final dehydrated and disintegrated tendon fibers had a shrink temperature $T_s$ in the range of 48° to 52° Centigrade.

EXAMPLE 4—HEXAMETHYLENEDIISOCYANATE CROSS-LINKING

Hexamethylenediisocyanate is a cross-linking agent in which the isocyanate group reacts with amino, amido, and quanidine groups of a polypeptide chain under the form of urea bonds, as indicated:

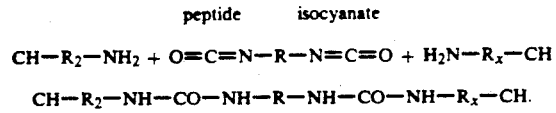

$T_s$ refers to shrinkage temperature, which indicates the structural stability or degree of cross linking of the treated collagen material. The above method has been developed as a direct result of the need for a collagen based bioprosthesis with minimal cytotoxicity and optimal biokinetics. Maximum emphasis has been placed on the prevention of formation of polyurethane crystals on the fibers being cross-linked. It must be emphasized that the starting fibers must be completely free of any foreign materials, such as crystals, salts, etc. The actual cross-linking reaction is carried out in a solvent system that prevents the native fibers from swelling beyond the desired degree. The solvent system is replaced at regular intervals to prevent the formation of urethane crystals during the HMDIC-water interaction. The optimal pH for the reaction is either a neutral or weak alkali. During the reaction the pH becomes acidic, due to the release of carboxyl groups. The hexamethylenediisocyanate (HMDIC) in aqueous medium metabolizes slowly to hexamethylenediamine, which condensates into polyurethane. While diamines are readily soluble in water, polyurethanes are insoluble in most solvents. Neither product is cytotoxic. However, polyurethane formation should be prevented as it forms a bond with the collagenous substrate, thus blocking and obscuring the desired cell-tissue interaction with collagen. The above-described method minimizes or prevents the formation of polyurethane crystals.

Cross-linking of pure collagen fibers obtained from Example 3 was accomplished by neutralizing the fibers in an excess of 60 volumes of acetone, 40 volumes of distilled, deionized water containing 0.5M NaHCO$_3$ for 60 minutes at room temperature on a slow shaker. Salt residue then was washed out in 60 volumes of acetone and 40 volumes of distilled, deionized water for 30 minutes at room temperature on a slow shaker, and repeated. The last wash of collagen fibers was in a solution containing 60 volumes of acetone, 20 volumes of glycerol, 40 volumes of acetone, and 20 volumes of distilled deionized water, for 60 minutes at room temperature. Cross linking was performed in 1.25 volumes of HMDIC dissolved in 40 volumes of glycerol, 40 volumes of acetone, and 20 volumes of distilled, deionized water with shaking to mix well the cross-linking substance, at room temperature. The solution was aspirated, and the collagen fibers were rinsed twice in 40 volumes of glycerol, 40 volumes of acetone, and 20 volumes of distilled, deionized water. The cross-linking procedure then was repeated. The solution was changed every 30 minutes for four hours and then every 60 minutes, with two rinses in 40 volumes of glycerol, 40 volumes of acetone, and 20 volumes of distilled, deionized water between every cross-linking cycle. The procedure is repeated for up to 14 hours or until the desired shrinkage temperature $T_s$ of 78° to 82° Centigrade is reached.

EXAMPLE 5—METHOD OF NEUTRALIZATION AND CROSS-LINKING BOVINE TENDON COLLAGEN FIBERS PRODUCED IN EXAMPLE 3

The purified fibers prepared according to Example 3 containing a pH of 3.5 and 20 weight percent NaCl were further neutralized by preparing a solution containing 20 weight percent NaCl and 0.5M phosphate buffer, with a pH of 5.5. The solution was incubated without shaking. The bundle of collagen fibers as shown in FIG. 1 were longitudinally oriented on a perforated screen wash by vertical movements of the screen in the solution. Due to the excess of NaCl content the fibers did not swell, but the pH was changed to less acidic. A cross-linking step, described in Example 4, was performed, preparing a 5 percent solution containing hexamethylenediisocyanate (HMDIC) in 20 volumes (i.e., units) of acetone and 80 volumes of phosphate buffer (pH of 5.5). The fibers were incubated approximately six hours until a shrinkage temperature ($T_s$) of approximately 80° Centigrade was obtained. Excess salt was removed by a solution containing 75 volumes of a phosphate buffer of 0.15M having a pH of 6.5, with 25 volumes of acetone. The collagen fibers were washed extensively at 4° Centigrade, with exchange of the bufferacetone solution. Once proper cross-linking was achieved, the collagen fibers were repeatedly rinsed in 0.15M phosphate buffer with a pH of 7.2. A commercially available tissue culture "medium 199" was used for impregnation of the final collagen fiber structure to increase fibrogenic cell invasion. The water from the longitudinally arranged collagen fibers was removed by a freeze drying process.

EXAMPLE 6—CROSS-LINKING BY MONOMERIC GLUTARALDEHYDE

This example shows that purified collagen fibers used to manufacture the tendon or ligament prosthesis can be cross-linked with another cross-linking agent than as in Examples 4 and 5 without adversely affecting the mechanical or biological characteristics of the collagen fibers. Many collagen based devices used in medicine, such as porcine heart valves, bovine pericardial heart valves or vascular prostheses of umbilical vein or artery are cross-linked by known processes using aldehydes, mainly glutaraldehyde, or formaldehyde (Nimmi U.S. Pat. No. 4,378,224). The existing procedures result in a product that after implantation in body tissues, such as heart or vessels, remains free of cells for several years due to the toxicity of the remaining glutaraldehyde or formaldehyde. The toxicity depends on the formation of polymers of glutaraldehyde, which are continuously and slowly hydrolyzed after in vivo implantation and which are toxic to cells. In this example I use only monomeric glutaraldehyde under defined conditions to eliminate the formation of the toxic residues fixed within the collagen product.

A commercially available glutaraldehyde solution at 25 weight percent concentration was diluted 50 times with deionized distilled water to form 0.5 percent final concentration. To 100 ml of such a diluted glutaraldehyde solution 10 grams of active charcoal (Norite) was added, well shaken and the solution was, after 10 minutes, filtered through dense filter paper. The filtered solution then contained only monomeric glutaraldehyde, which was shown by obtaining only one absorption peak at 280 nm in an ultraviolet spectroscopic scan. Thus, charcoal absorbed all of the polymeric glutaraldehyde present in all commercially available samples, giving a strong absorption maximum at 235 nm. By eliminating the polymeric glutaraldehyde through charcoal filtration the residual concentration of monomeric glutaraldehyde was about 0.20–0.25 percent (solution A). In the following step the solution of monomeric glutaraldehyde was mixed with an acetate buffer (0.1M) having the pH 4.5 to obtain final concentration of glutaraldehyde 0.15–0.20 percent (solution B). The collagen fibers then were incubated in excess of this solution for 60 minutes at 4° Centigrade, the fibers being not stirred to avoid knot formation. In the next step, solution A was diluted with Tris buffer (0.1M) pH 6.5 to form final concentration of glutaraldehyde 0.15–0.20 percent (solution C). Collagen fibers were then taken from solution B, blotted on filter paper and transferred into solution C for 180 minutes at 4° Centigrade. After this time fresh solution C were made and fibers transferred in the fresh solution for additional 120 minutes, and incubated at 20° Centigrade. The extracts were checked for the presence of glutaraldehyde by UV spectroscopy. The washing was terminated only when no more leachable glutaraldehyde was present. A final wash was in tissue culture medium called "minimum essential medium" (MEM) used in tissue culture methodology. The fibers were dried by a freeze drying procedure. The final fibers had a shrink temperature of 78 degrees to 80 degrees Centigrade and retained 40 weight percent water.

EXAMPLE 7

This example shows that sterilization of the final implant product by gamma radiation is an acceptable method and does not induce any change in the structural stability of the cross-linked collagen fibers.

The final product, in the form of braided collagen fibers, cross-linked according to the process described in Examples 4 and 7 was submitted to a sterilization dose of gamma radiation of an average dose of 2.5 Merads with an 0.5 Merad possible deviation from the average requested value. The original collagen fibers comprising the ligament product were cross-linked to a degree corresponding to 83.5° Centigrade shrinkage temperature. After the sterilization, the shown dose of gamma radiation was found to have no effect on the structural stability of the collagen as no change from the original shrink temperature was found.

While the invention has been described with reference to a particular embodiment thereof, those skilled in the art will be able to make various modifications to the described embodiment of the invention without departing from the true spirit and scope thereof. It is intended that all elements and steps which perform substantially the same function in substantially the same manner to achieve the same result are within the scope of the invention. For example, a few of the fibers in an implant might be composed of material other than animal ligament or tendon fibers, i.e. dacron, polyurethane, polytetrafluroethylene, pyrolized carbon, etc., to provide increased strength of the implant. Other cell proliferation promoting substances than fibronectin such as "fibroblast growth factor" and "angiogenesis factor" may be used.

I claim:

1. A method of regrowing natural anterior cruciate ligament connective tissue in place of damaged connective tissue of a joint in a subject, the method comprising the steps of:
   (a) providing purified individual long, thin connective animal tendon or ligament tissue fibers;
   (b) cross-linking the connective animal tissue fibers so as to produce a shrinkage temperature of the fibers of approximately 75 degrees to 85 degrees centigrade and so that the tensile strength of the fibers is approximately four to eight kilograms per square millimeter;
   (c) forming an elongated heterograft of the fibers by forming each of a plurality of groups by arranging a plurality of the fibers in close, generally parallel relationship to each other, and then positioning the groups generally in the direction of a longitudinal axis of the heterograft, so that each of the fibers extends from one end of the heterograft to the other;

(d) replacing at least a part of the damaged connective tissue with the heterograft so that the fibers are oriented in generally the same direction as fibers of the damaged connective tissue before it was damaged, thereby causing ingrowth of fibrogenic cells along the connective animal tissue fibers and ingrowth of host connective tissue by the ingrowing fibrogenic cells, the cross-linking being sufficient to cause resorption of the heterograft at a rate such that the sum of decreasing tensile strength of the heterograft and increasing tensile strength of ingrown host connective tissue never is less than approximately an original tensile strength of the damaged connective tissue before it was damaged; and (e) soon after step (d), causing the subject to repetitively apply certain normal stress to the heterograft to align fibrogenic cells and natural collagen tissue produced by the fibrogenic cells in the direction of the stress, to thereby orient and enhance growth of the natural connective tissue to thereby replace the damaged connective tissue.

2. A method of regrowing natural connective tissue in place of damaged connective tissue of a subject, the method comprising the steps of:

(a) providing purified individual long, thin connective animal tendon or ligament tissue fibers;

(b) cross-linking the connective animal tissue fibers so as to produce a shrinkage temperature of the fibers of approximately 75 degrees to 85 degrees centigrade and so that the tensile strength of the fibers is approximately four to eight kilograms per square millimeter;

(c) forming an elongated heterograft of the fibers by forming each of a plurality of groups by arranging a plurality of the fibers in close, generally parallel relationship to each other, and then positioning the groups generally in the direction of a longitudinal axis of the heterograft, so that each of the fibers extends from one end of the heterograft to the other;

(d) replacing at least a part of the damaged connective tissue with the heterograft so that the fibers are oriented in generally the same direction as fibers of the damaged connective tissue before it was damaged, thereby causing ingrowth of fibrogenic cells along the connective animal tissue fibers and ingrowth of host connective tissue by the ingrowing fibrogenic cells, the cross-linking being sufficient to cause resorption of the heterograft at a rate such that the sum of decreasing tensile strength of the heterograft and increasing tensile strength of ingrown host connective tissue never is less than approximately an original tensile strength of the damaged connective tissue before it was damaged; and (e) soon after step (d), causing the subject to repetitively apply certain normal stress to the heterograft to align fibrogenic cells and natural collagen tissue produced by the fibrogenic cells in the direction of the stress, to thereby orient and enhance growth of the natural connective tissue to thereby replace the damaged connective tissue.

3. A method of regrowing natural connective tissue in place of damaged connective tissue of a subject, the method comprising the steps of:

(a) providing purified individual long, thin connective animal tendon or ligament tissue fibers;

(b) cross-linking the connective animal tissue fibers so as to produce a shrinkage temperature of the fibers of approximately 75 degrees to 85 degrees centigrade;

(c) forming an elongated heterograft of the fibers by forming each of a plurality of groups by arranging a plurality of the fibers in close, generally parallel relationship to each other, and then positioning the groups generally in the direction of a longitudinal axis of the heterograft, so that each of the fibers extends from one end of the heterograft to the other, the cross-linking causing the initial tensile strength of the heterograft to be at least equal to approximately the original tensile strength of the damaged connective tissue being replaced;

(d) replacing at least a part of the damaged connective tissue with the heterograft so that the fibers are oriented in generally the same direction as fibers of the damaged connective tissue before it was damaged, thereby causing ingrowth of fibrogenic cells along the connective animal tissue fibers and ingrowth of host connective tissue by the ingrowing fibrogenic cells, the cross-linking being sufficient to cause resorption of the heterograft at a rate such that the sum of decreasing tensile strength of the heterograft and increasing tensile strength of ingrown host connective tissue never is less than approximately an original tensile strength of the damaged connective tissue before it was damaged; and (e) soon after step (d), causing the subject to repetitively apply certain normal stress to the heterograft to align fibrogenic cells and natural collagen tissue produced by the fibrogenic cells in the direction of the stress, to thereby orient and enhance growth of the natural connective tissue to thereby replace the damaged connective tissue.

4. A method of regrowing natural connective tissue in place of damaged connective tissue of a subject, the method comprising the steps of:

(a) providing purified individual long, thin connective animal tendon or ligament tissue fibers;

(b) cross-linking the connective animal tissue fibers so as to produce a shrinkage temperature of the fibers of approximately 75 degrees to 85 degrees centigrade and so that the tensile strength of the fibers is approximately four to eight kilograms per square millimeter;

(c) forming an elongated heterograft of the fibers by forming each of a plurality of groups by arranging a plurality of the fibers in close, generally parallel relationship to each other, and then positioning the groups generally in the direction of a longitudinal axis of the heterograft;

(d) replacing at least a part of the damaged connective tissue with the heterograft so that the fibers are oriented in generally the same direction as fibers of the damaged connective tissue before it was damaged, thereby causing ingrowth of fibrogenic cells along the connective animal tissue fibers and ingrowth of host connective tissue by the ingrowing fibrogenic cells, the cross-linking being sufficient to cause resorption of the heterograft at a rate such that the sum of decreasing tensile strength of the heterograft and increasing tensile strength of ingrown host connective tissue never is less than approximately an original tensile strength of the damaged connective tissue before it was damaged; and (e) soon after step (d), causing the subject to repetitively apply certain normal stress to the heterograft to align fibrogenic cells and natural collagen tissue produced by the fibrogenic cells in the direction of the stress, to thereby orient and enhance growth of the natural connective tissue to thereby replace the damaged connective tissue.

5. The method of claim 1 wherein step (e) includes allowing free movement of the joint to which the damaged connective tissue was originally connected and causing the subject to carry out certain normal physical activities using the joint.

6. The method of claim 5 wherein step (c) includes providing a sufficient number of the connective animal tissue fibers in the heterograft to cause the tensile strength of the heterograft to withstand stress produced by the activities.

7. The method of claim 6 wherein the heterograft has compliance approximately equal to the compliance of the damaged connective tissue before it was damaged, whereby step (e) includes stressing the natural connective tissue produced by the fibrogenic cells to approximately the same extent that the original connective tissue would have been stressed by the activities before it was damaged.

8. The method of claim 1 wherein the damaged connective tissue is ligament tissue, step (d) includes drilling a hole in alignment with the original ligament, passing a part of the heterograft through the hole, passing a portion of the heterograft through an incision in periarticular connective tissue of the joint, suturing the periarticular connective tissue to the heterograft, and fastening an end portion of the heterograft to periosteum tissue of the joint.

9. The method of claim 1 wherein step (c) includes doubling sections of each fiber back on itself to form loops at at least one end of the heterograft, and suturing that end of the heterograft to a stump of the connective tissue fiber by passing sutures through the loops and the damaged connective tissue stump.

10. The method of claim 8 wherein step (d) includes anchoring the heterograft to a member of the joint by inserting a bone wedge into the drilled hole to wedge a portion of the heterograft therein.

11. The method of claim 1 wherein the damaged connective tissue is tendon tissue contained in a peritendinous sheath, the method including making an incision in the peritendinous sheath before step (d), and suturing the incision after step (d), and step (c) includes arranging the connective animal tissue fibers to produce loops at opposite ends of the heterograft, and suturing the ends of the heterografts to adjacent stumps of the damaged connective tissue by passing sutures through the loops at each end of the heterograft and through the adjacent tendon stumps.

12. The method of claim 1 wherein step (c) includes arranging the connective animal tissue fibers in a pattern that closely approximates the pattern of bundles of collagen fibers contained in the connective tissue before it was damaged, to thereby cause regrowth of the natural connective tissue in the same pattern.

13. The method of claim 1 wherein step (d) includes coating the connective animal tissue fibers with material containing cell proliferation promoting factors.

14. The method of claim 13 wherein the cell proliferation promoting factors include angiogenesis factor.

15. The method of claim 1 wherein step (b) includes cross-linking the connective animal tissue fibers with hexamethylenediisocyanate.

16. The method of claim 1 wherein the preselected shrinkage temperature is selected to prevent complete resorption of the heterograft in less than approximately six months after step (d).

17. The method of claim 1 wherein step (c) includes braiding the connective animal tissue fibers to form the heterograft with a selected length and a selected thickness.

18. The method of claim 1 wherein step (c) includes interlacing the groups along the longitudinal axis.

19. The method of claim 2 wherein step (c) includes interlacing the groups along the longitudinal axis.

* * * * *